United States Patent [19]

Desmurs et al.

[11] Patent Number: 5,105,027
[45] Date of Patent: Apr. 14, 1992

[54] CATALYTIC/CO-CATALYTIC PRODUCTION OF BISPHENOL A

[75] Inventors: Jean-Roger Desmurs, St. Symphorien D'Ozon; Francis Pierre, Lyons, both of France

[73] Assignee: Rhone-Poulenc Chimie, Courbevoie, France

[21] Appl. No.: 661,817

[22] Filed: Feb. 28, 1991

[30] Foreign Application Priority Data

Feb. 28, 1990 [FR] France ............... 90 02758

[51] Int. Cl.$^5$ ............... C07C 37/20; C07C 39/16
[52] U.S. Cl. ............... 568/727; 568/722; 568/728
[58] Field of Search ............... 568/727, 722, 728

[56] References Cited

U.S. PATENT DOCUMENTS

| | | | |
|---|---|---|---|
| 4,052,466 | 10/1977 | Sun | 568/727 |
| 4,053,522 | 10/1977 | McClure et al. | 568/727 |
| 4,317,944 | 3/1982 | Davis | 568/727 |
| 4,387,251 | 6/1983 | Meyer et al. | 568/727 |
| 4,918,245 | 4/1990 | Iimuro et al. | 568/727 |

*Primary Examiner*—Werren B. Lone
*Attorney, Agent, or Firm*—Burns, Doane, Swecker & Mathis

[57] ABSTRACT

Bisphenol A is prepared by condensing a stoichiometric excess of phenol with acetone in the presence of (a) a catalytically effective amount of an acid catalyst, e.g., benzenesulfonic acid, and (b) a co-catalytically effective amount of a functional polymer characteristically having the formula:

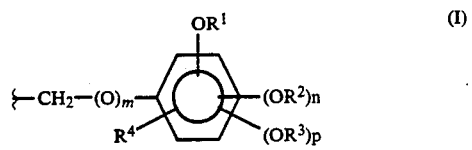

(I)

in which m is 0 or 1, n is 0 or 1, p is 0 or 1, $R^1$, $R^2$ and $R^3$, which may be identical or different, are each a hydrogen atom, a $C_1$–$C_6$ alkyl radical or a phenyl radical optionally substituted by 1 or 2 hydroxyl or $C_1$–$C_4$ alkoxy groups, and $R^4$ is a hydrogen atom, a halogen atom, a $C_1$–$C_6$ alkyl radical, or one of the groups: —CHO, —NO$_2$, —CO$_2$H, —CO$_2$R$^5$ wherein $R^5$ is a $C_1$–$C_4$ alkyl radical, or

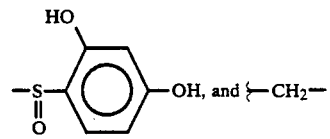

is the residue of a chloromethylated resin.

17 Claims, 1 Drawing Sheet

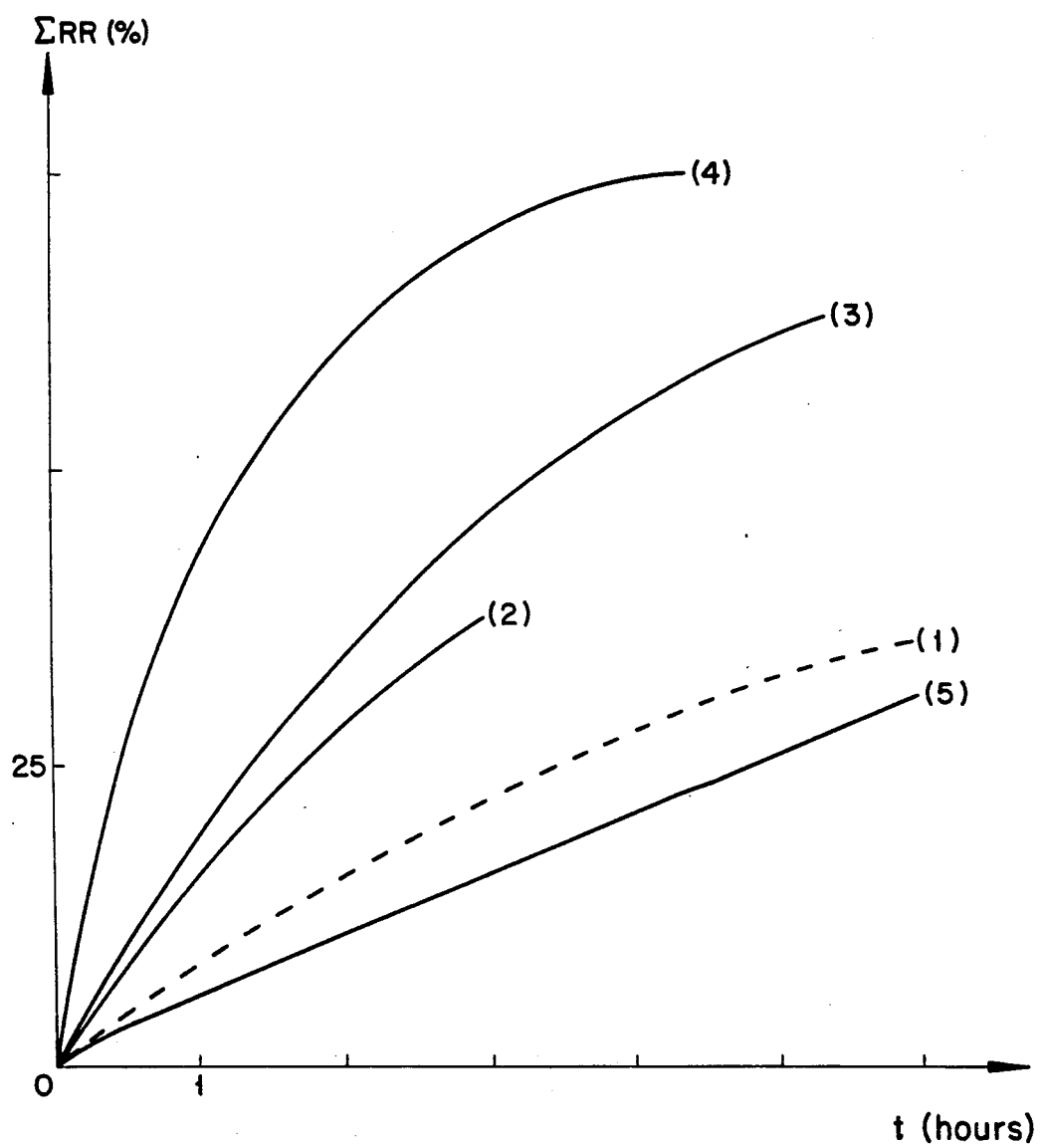

CATALYTIC/CO-CATALYTIC PRODUCTION OF BISPHENOL A

BACKGROUND OF THE INVENTION

1. Field of the Invention

The present invention relates to the preparation of bisphenol A by a condensation reaction of phenol and acetone, and, more especially, to the preparation of bisphenol A by condensing phenol with acetone in the presence of an acid catalyst and a particular polymer additive or co-catalyst.

2. Description of the Prior Art

Bisphenol A or 2,2-bis(4-hydroxyphenyl)-propane is a valuable intermediate known to be useful in the production of epoxy and polycarbonate resins.

Numerous processes for the production of bisphenol A are known to this art. The most widely known comprises the reaction of acetone with an excess of phenol in the presence of an acid catalyst at temperatures on the order of 30° to 80° C.

The catalyst can be a solid or liquid inorganic acid, such as a clay, aluminum trichloride, hydrochloric acid or sulfuric acid, or an organic acid such as benzenesulfonic acid (cf. published Japanese Application 62-5926 and U.S. Pat. No. 4,387,251), or an ion exchange resin (c. AIChEJ, 20 (5), pp 933–40 (1974)).

The processes using heterogenous catalysts present the major disadvantages of necessitating operation at a low bisphenol A concentration, such as to prevent the precipitation of the complex (bisphenol A/phenol), or at higher temperatures, which promote the formation of by-products. It is for these reasons that, more preferably, an acid soluble in the reaction mixture is used, such as hydrochloric acid. Hydrochloric acid, in turn, presents the major disadvantage of necessitating reactors which are made of materials capable of resisting extensive corrosion; therefore, they are very expensive. As the majority of the other acids are less active than hydrochloric acid, the contact times must be increased to obtain an acceptable or complete degree of conversion of the acetone. However, such an increase in the contact time is reflected in the appearance of particularly undesirable parasitic species such as 2-(o-hydroxyphenyl)-2-(p-hydroxyphenyl)propane (o,p′isomer of bisphenol A), 2,2,4-trimethyl-4-(p-hydroxyphenyl)-chromane or codimer, and higher condensation products such as trisphenol. These species can be separated from the bisphenol A only by a succession of purification steps which are often difficult to carry out and are always relatively costly.

Moreover, for certain applications, it is imperative that the bisphenol A has no coloration whatsoever and has a very high degree of purity. This is the case, in particular, when using the bisphenol A for the synthesis of polycarbonate resins, in which the presence of foreign substances has a pronounced inhibitory effect.

In this regard, it has already been proposed to this art to add a "co-catalyst" or additive to the (phenol/acetone/acid catalyst) system.

The co-catalyst is most typically a sulfur compound such as an alkyl mercaptan (cf. Netherlands Patent Application No. 73/09,229), an alkylmercaptocarboxylic or -sulfonic acid (cf. Australian Patent No. 474,155 and French Patent No. 1,179,377) or an amino alkanethiol (cf. Japanese Patent Application No. 74/20,565).

However, the use of these accelerators does not prove fully advantageous: they still present serious difficulties in treatment for their removal and/or their recovery and they often impart an undesired odor to the final product.

The use of another class of "co-catalysts" has been described in U.S. Pat. No. 4,052,466, i.e., poly(hydroxy)benzene derivatives, in particular resorcinol and the monomethyl or dimethyl ethers thereof, which are used in an amount of 0.1% to 10 mole % relative to the phenol employed. These derivatives provide results similar to those obtained with, for example, the mercaptans. Indeed, they activate the phenol/acetone condensation reaction in the presence of an acid catalyst and tend to reduce the parasitic chemistry.

However, these derivatives reflect the major drawback of pursuing the same route as the organic impurities of bisphenol A in the production chain. They have an adverse influence on the crystallization of the bisphenol A/phenol adduct and remain present, at least in trace amounts, in the final product.

In such context, it will be appreciated that serious need exists in this art for additives which are capable of activating the condensation reaction of phenol and acetone without promoting parasitic competing reactions and which proceed by a mechanism different from that of the impurities and/or bisphenol A in the production chain.

SUMMARY OF THE INVENTION

Accordingly, a major object of the present invention is the provision of an improved process for the preparation of bisphenol A by condensation of excess phenol with acetone in the presence of an acid catalyst and of an additive or co-catalyst therefor, said additive having the formula (I):

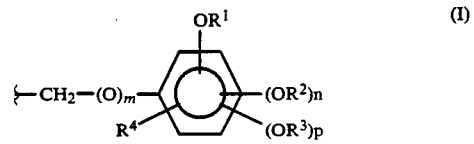

in which m is 0 or 1; n is 0 or 1; p is 0 or 1; $R^1$, $R^2$ and $R^3$, which may be identical or different, are each a hydrogen atom, a $C_1$–$C_6$ alkyl radical or a phenyl radical optionally substituted by 1 or 2 hydroxyl or $C_1$–$C_4$ alkoxy groups; $R^4$ is a hydrogen atom, a halogen atom, a $C_1$–$C_6$ alkyl radical or one of the groups —CHO, —$NO_2$, —$CO_2H$, —$CO_2R^5$ wherein $R^5$ is a $C_1$–$C_4$ alkyl radical, or

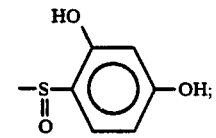

and

is a residue of a chloromethylated resin.

DESCRIPTION OF THE DRAWING

This illustrates the results obtained in Examples 8–10 as well as Control Experiments (b) and (c).

DETAILED DESCRIPTION OF THE PREFERRED EMBODIMENTS OF THE INVENTION

More particularly according to the present invention, in formula (I), when $R^4$ is a halogen atom, it is preferably chlorine or bromine.

The chloromethylated resin from which the additive is derived is of the "polystyrene/divinylbenzene" type in which the proportion of divinylbenzene is greater than or equal to 6%. The following are exemplary such resins suitable for carrying out the process of the invention: the BIO-BEAD® S-X1 resins from Biorad and the DUOLITE® LES 9001 and DUOLITE® LES 3781 resins marketed by ROHM and HAAS.

The resins which are in the form of beads are more particularly preferred for carrying out the process of this invention.

To satisfactorily carry out the process of the invention, at least 90% of the chlorine atoms in the chloromethylated resin will be replaced by a group (or graft) of formula (II):

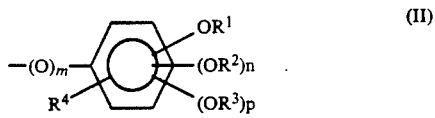

in which n, m, p and $R^1$ to $R^4$ are as defined above.

The above additives can be prepared by transposition of one or another of the methods described, respectively, in:

(1) K. A. Kun, *J. of Polymer Science*, Part A, vol. 3, pp 1833–43 (1965);

(2) Doctoral Thesis of T. D. Nguyen, dated Oct. 21, 1981, P & M CURIE University, Paris 6, France.

In accordance with the method described in publication (1), additives of formula (I) will be obtained in which m is 0; in accordance with the method described in thesis (2), additives of the formula (I) will be obtained in which m is 1; the additives for which m is 0 are the preferred.

In summary, the method described in (1) comprises the reaction of diphenol with the chloromethylated resin in dry dioxane, under reflux, in the presence of anhydrous zinc chloride; the method described in (2) comprises the reaction of the corresponding phenate with the chloromethylated resin under conditions of phase transfer catalysis, namely, in dimethylformamide, at 60° C. in the presence of aqueous sodium hydroxide solution and tetrabutylammonium hydrogen sulfate.

The above radicals of formula (II) result from the removal of a hydrogen atom from a disubstituted or polysubstituted aromatic compound.

The following are exemplary such aromatic compounds: resorcinol, pyrrogallol, 2-bromoresorcinol, 2,6-dihydroxybenzoic acid and the methyl ester thereof, 2,4-dihydroxybenzaldehyde, bis(2,4-dihydroxyphenyl)sulfoxide, resorcinol monomethyl ether and 4-(n-hexyl)resorcinol.

Preferably, additives of the formula (I) are used, in which:

m is zero;

$R^4$ is a hydrogen atom or a $C_2$–$C_6$ alkyl radical;

$R^1$, $R^2$ and $R^3$, which may be identical or different, are each a hydrogen atom or a $C_1$–$C_4$ alkyl radical.

To satisfactorily carry out the process of the invention, the additives correspond to the formula (I) in which at least one of the radicals $R^1$ to $R^3$ is a hydrogen atom and the other two, which may be identical or different, are each a hydrogen atom or a methyl radical.

Particularly advantageous additives correspond to the formula (I) in which:

m is zero;

p is zero;

$R^4$ is a hydrogen atom or a $C_1$–$C_6$ alkyl radical; and the two radicals $R^1$ and $R^2$ are each a hydrogen atom, and the hydroxyl groups thus present are in positions 2- and 4- on the aromatic ring relative to the methylene bridge.

The amount of additive to be used is not critical In general, an amount of additive will be used such that the molar ratio of the radicals of formula (II) above to acetone ranges from 0.1 to 3 and preferably from 0.5 to 1.5.

As indicated above, the condensation reaction of phenol and acetone is carried out in the presence of an acid catalyst. Any type of acid is suitable, provided, of course, that it does not degrade the resin constituting the co-catalyst, and that is not introduced onto the aromatic ring of the graft.

Exemplary such acid catalysts include inorganic acids such as HClO or organic acids such as methanesulfonic acid, benzenesulfonic acid and the resins bearing sulfonic acid groups.

Benzenesulfonic acid is especially preferred for carrying out the process of this invention.

The amount of such acid is typically at least 0.1 mole per mole of acetone; it preferably ranges from 0.2 to 0.5 mole per mole of acetone.

The reaction is conducted with an excess of phenol. The molar ratio of phenol/acetone advantageously ranges from 2 to 16 and preferably from 8 to 12.

The condensation reaction of phenol with acetone is carried out at a temperature higher than 30° C. in order to obtain a reasonable activity and at below 120° C., above which temperature the additive is liable to degrade and parasitic competing reactions might interfere with the quality of the desired condensation.

The process according to the invention is satisfactorily carried out at a temperature ranging from 30° to 80° C.

Upon completion of the reaction or at the end of the time period permitted therefor, the reaction mixture is filtered and the co-catalyst is then recovered. After washing with phenol, this co-catalyst can be reemployed in a new condensation operation. The filtrate, containing bisphenol A, phenol and any acetone which has not reacted, is subjected in a manner known per se to treatment (distillation, flashing, etc.) to recover the bisphenol A.

In order to further illustrate the present invention and the advantages thereof, the following specific examples are given, it being understood that same are intended only as illustrate and in nowise limitative.

EXAMPLES 1 TO 3

Processing of chloromethylated resins

A volume of 50 ml of test resin was placed in a chromatography column; 500 ml of methanol divided into 3 portions of respectively, 100 ml, 100 ml and 300 ml, were permitted to slowly run therethrough. The resin was then dried in an oven at 70° C. under vacuum (about 100 torr) for 12 hours.

The following 3 samples were treated in accordance with the method described above:

EXAMPLE 1: DUOLITE ® LES 9001, chloromethylated resin marketed by ROHM and HAAS.
EXAMPLE 2: DUOLITE ® LES 3781, chloromethylated resin marketed by ROHM and HAAS.
EXAMPLE 3: BIO-BEADS ® S-X1, chloromethylated resin marketed by BIORAD.

The water and chlorine analyses of these resins provided the following results:

| | Support resin | | |
|---|---|---|---|
| | 1 Duolite LES-3781 | Duolite LES-3781 | 23 Bio-Beads S-X1 |
| % H$_2$O (Karl-Fischer) | 0.002 | 0.06 | 0.057 |
| % Cl (meq. Cl/g) | 21.77 (6.14) | 20.21 (5.70) | 14.89 (4.20) |
| particle size | 18–35 mesh (500–1000 μm) | 18–35 mesh (500–1000 μm) | 200–400 mesh (37–74 μm) |

EXAMPLE 4

C-Alkylation of Duolite LES-9001 resin by resorcinol 10 g of Duolite LES-9001 resin (treated in Example 1) (61.4 meq of Cl), 70 ml of dioxane dried on a 5 Å sieve and 10.14 g of resorcinol (91,.1 mmols) were introduced into a 250 ml round-bottomed flask fitted with a condenser, a thermometer, an argon inlet and a magnetic stirrer. After stirring for ten minutes, 0.40 g of freshly melted zinc chloride (2.93 mmol) were added. The reaction mixture was refluxed for 24 hours. After cooling to 70° C., the resin was filtered off and then washed at ambient temperature with 2×100 ml of dioxane and then with 3×50 ml of ethanol. The resin was then purified by extraction with methanol for 24 hours and was dried under vacuum (100 torr) at 45°–50° C. 11.39 g of resin were recovered, the analyses of which provided the results below:

| | DUOLITE LES 9001 |
|---|---|
| % H$_2$O | 1.65 |
| % Cl | 0.35 |
| %0 | 11.19 |
| Particle size | 18–35 mesh (500–1000 μm) |

This corresponded to a resorcinol content of 4.1 mmols per gram of resin.

EXAMPLE 5

C-Alkylation of BIO-BEADS S-X1 resin by resorcinol

The procedure of Example 4 was repeated, but charging:
(i) 8.25 g of BIO-BEADS S-X1 resin (treated in Example 3);
(ii) 5.72 g of resorcinol;
(iii) 0.23 of freshly melted zinc chloride; and
(iv) 80 ml of dioxane on a 5 Å sieve
9.4 g of resin were recovered, the analyses of which provided the following results:

| | BIO-BEADS S-X1 RESIN |
|---|---|
| % H$_2$O | 0.5 |
| % Cl | 0.27 |
| %0 | 6.67 |

| | BIO-BEADS S-X1 RESIN |
|---|---|
| Particle size | 150–290 mesh (49–97 μm) |

These analyses corresponded to a resorcinol content of 3.13 mmols per gram of resin.

EXAMPLE 6

C-Alkylation of DUOLITE LES 3781 resin by resorcinol

The procedure of Example 4 was repeated, but charging:
(i) 10 g of DUOLITE LES 3781 resin (treated in Example 2);
(ii) 9.41 g of resorcinol;
(iii) 0.37 g of freshly melted zinc chloride; and
(iv) 65 ml of dioxane.
10.25 g of resin were recovered, the analysis of which provided the following results:

| | DUOLITE S-X1 RESIN |
|---|---|
| % H$_2$O | 1.2 |
| % Cl | 2 |
| %0 | 8.52 |
| Particle size | 18–35 mesh (500–1000 μm) |

These analyses corresponded to a resorcinol content of 3.57 mmols per gram of resin.

Control Experiment (a)

C-Alkylation of DUOLITE LES 9001 resin by phenol

The procedure of Example 4 was repeated, but charging
(i) 10 g of DUOLITE LES 9001 resin (treated in Example 1);
(ii) 8.67 g of phenol;
(iii) 0.40 g of freshly melted zinc chloride; and
(iv) 70 ml of sieve-dried dioxane.
10.8 g of resin were recovered, the analyses of which provided the following results:

| | DUOLITE LES 9001 RESIN |
|---|---|
| % H$_2$O | 1.02 |
| % Cl | 1.04 |
| %0 | 5.91 |
| Particle size | 18–35 mesh (500–1000 μm) |

These analyses corresponded to a phenol content of 4.27 mmols of phenol per g of resin.

EXAMPLE 7

O-Alkylation of DUOLITE LES 9001 resin 5 g of DUOLITE LES 9001 resin (treated in Example 1) and 150 ml of DMF were charged into a 250 ml round-bottomed flask fitted with a condenser, a thermometer, an argon inlet and a magnetic stirrer. After having swollen the resin for 42 hours at ambient temperature, 0.51 g of tetrabutylammonium hydrogen sulfate, 4 ml of 50% aqueous sodium hydroxide solution and 6.67 g of resorcinol were added. The reaction mixture was heated for six hours at 65° C. The resin was then filtered off, washed with 5×250 ml of water and 3×250 ml of methanol and then dried.

5.03 g of resin were recovered, the analyses of which provided the following results:

|  | 0-ALKYLATED DUOLITE |
|---|---|
| % H₂O | 3.5 |
| % Cl | 4.38 |
| %0 | 6.2 |
| Particle size | 18-35 mesh (500-1000 μm) |

These analyses corresponded to a resorcinol content of 2.54 mmols per gram of resin.

Control Experiment (b)

Synthesis of bisphenol A catalyzed by benzenesulfonic acid 7.56 g of phenol (0.08 mol) and 0.56 g of benzenesulfonic acid (0.0035 mol) were charged into a 30 ml reactor fitted with a magnetic stirrer. This mixture was heated to 50° C. When the temperature of the reactor had stabilized at 50° C., 0.58 g of acetone (0.01 mol) was introduced very rapidly with the aid of a syringe. Samples withdrawn at various time intervals were assayed by high performance liquid chromatography to determine the yields of bisphenol A and impurities.

The results obtained are reported in Table I below, in which the following conventions are used.

The yields are indicated with respect to the acetone employed for the various products, as follows:

pp' for the p,p' isomer of bisphenol A,
op' for the o,p' isomer of bisphenol A,
BPX for trisphenol,
Codimer for 2,2,4-trimethyl-4(p-hydroxyphenyl)-chromane,
Spiro for 6,6'-dihydroxy-3,3,3',3'-tetramethyl-1,1'-spiro-biindane,
ΣYY represents the sum of the yields obtained for the o, p' and p, p' isomers of bisphenol A,
Q represents the proportion of o, p' isomer int he mixture of o, p' and p, p' isomers of bisphenol A

TABLE I

| Time (h) | pp' | op' | BPX | Codimer | Spiro | ΣYY | Q |
|---|---|---|---|---|---|---|---|
| 0.25 | 1.17 | 0.58 | — | — | — | 1.75 | 0.333 |
| 0.50 | 2.97 | 1.32 | — | — | — | 4.29 | 0.307 |
| 1.00 | 6.10 | 2.64 | 0.06 | 0.26 | — | 8.74 | 0.302 |
| 2.00 | 11.90 | 4.59 | 0.31 | 0.71 | — | 16.49 | 0.279 |
| 3.58 | 19.10 | 6.56 | 0.52 | 1.74 | 0.10 | 25.66 | 0.255 |
| 4.67 | 23.63 | 7.47 | 0.78 | 2.13 | 0.14 | 31.10 | 0.240 |
| 5.50 | 26.74 | 7.91 | 0.82 | 2.45 | 0.11 | 34.65 | 0.228 |
| 6.67 | 29.61 | 8.45 | 1.00 | 2.84 | 0.25 | 38.06 | 0.222 |

EXAMPLE 8

Synthesis of bisphenol A catalyzed by benzenesulfonic acid int eh presence of DUOLITE LES 9001 resin C-alkylated by resorcinol 7.56 g of phenol (0.08 mol) and 0.56 g of benzenesulfonic acid (0.0035 mol) and 2.5 g of the resin prepared according to Example 4 (0.01 mol of resorcinol) were charged into a 30 ml reactor fitted with a magnetic stirrer. The reaction mixture was heated to 50°. When the temperature of the reaction mixture had reached 50° C., 0.58 g of acetone (0.01 mol) was introduced very rapidly with the aid of a syringe. Samples withdrawn at various time intervals were assayed by high performance liquid chromatography to determined the yields of bisphenol A and impurities.

The results obtained are reported in Table II below, in which the conventions used are those defined above for Control Experiment (b).

TABLE II

| Time (h) | pp' | op' | BPX | Codimer | Spiro | ΣYY | Q |
|---|---|---|---|---|---|---|---|
| 0.084 | 0.53 | 0.21 | 0.01 | — | — | 0.74 | 0.282 |
| 0.25 | 4.7 | 0.92 | 0.11 | — | — | 5.62 | 0.163 |
| 0.50 | 9.2 | 1.50 | 0.10 | — | — | 10.70 | 0.142 |
| 1.17 | 19.84 | 2.44 | 0.25 | 0.07 | — | 22.30 | 0.111 |
| 2.17 | 32.54 | 3.74 | 0.70 | 0.21 | 0.07 | 36.29 | 0.103 |
| 4.33 | 50.32 | 5.27 | 1.43 | 0.36 | 0.10 | 55.60 | 0.095 |
| 5.42 | 64.05 | 5.71 | 1.55 | 0.37 | 0.15 | 69.76 | 0.082 |
| 8.18 | 90.38 | 5.83 | 1.42 | 0.74 | 0.17 | 96.21 | 0.060 |

EXAMPLE 9

Synthesis of bisphenol A catalyzed by benzenesulfonic acid int eh presence of BIO BEADS S-X1 resin C-alkylated by resorcinol The procedure of Example 8 was repeated, using the following reagents:
(i) 7.56 g of phenol (0.08 mol);
(ii) 0.58 g of acetone (0.01 mol);
(iii) 0.56 g of benzenesulfonic acid (0.0035 mol); and
(iv) 3.2 g of the resin prepared according to Example 5 (0.01 mol of resorcinol).

The analyses of the various samples evidenced much more rapid kinetics.

The results obtained are reported in Table III below, in which the conventions used are those defined above for Control Experiment (b).

TABLE III

| Time (h) | pp' | op' | BPX | Codimer | Spiro | ΣYY | Q |
|---|---|---|---|---|---|---|---|
| 0.084 | 7.10 | 0.76 | 0.11 | — | — | 7.86 | 0.096 |
| 0.25 | 15.06 | 1.27 | 0.15 | — | — | 16.33 | 0.078 |
| 0.62 | 30.76 | 2.27 | 0.46 | — | — | 33.03 | 0.069 |
| 1.25 | 46.53 | 3.38 | 1.06 | 0.07 | 0.12 | 49.91 | 0.068 |
| 4.42 | 71.03 | 4.46 | 1.48 | 0.10 | 0.14 | 75.49 | 0.05 |

EXAMPLE 10

Synthesis of bisphenol A catalyzed by benzenesulfonic acid in the presence of DUOLITE LES 3781 resin C-alkylated by resorcinol The procedure of Example 8 was repeated, using the following reagents:
(i) 7.56 g of phenol (0.08 mol);
(ii) 0.58 g of acetone (0.01 mol);
(iii) 0.56 g of benzenesulfonic acid (0.0035 mol); and
(iv) 1.63 g of the resin prepared according to Example 6 (0.01 mol of resorcinol)

The analyses of the samples evidenced a perceptible increase in the reaction kinetics.

The results obtained are reported in Table IV below, in which the conventions used are those defined above for Control Experiment (b).

TABLE IV

| Time (h) | pp' | op' | BPX | Codimer | Spiro | ΣYY | Q |
|---|---|---|---|---|---|---|---|
| 0.25 | 0.74 | 0.65 | 0.04 | — | — | 1.39 | 0.468 |
| 0.50 | 3.03 | 1.39 | 0.09 | 0.09 | — | 4.42 | 0.314 |
| 1.00 | 7.81 | 3.34 | 0.16 | 0.28 | — | 11.15 | 0.299 |
| 2.00 | 17.64 | 6.15 | 0.59 | 0.87 | 0.02 | 23.79 | 0.258 |
| 3.42 | 31.00 | 8.15 | 1.24 | 0.95 | 0.07 | 39.15 | 0.208 |
| 4.50 | 43.78 | 8.47 | 1.74 | 1.36 | 0.11 | 52.25 | 0.162 |
| 5.83 | 66.92 | 7.76 | 1.08 | 1.52 | 0.22 | 74.68 | 0.104 |
| 7.34 | 86.65 | 4.91 | 0.62 | 2.04 | 0.25 | 91.56 | 0.054 |

Control Experiment (c)

Synthesis of bisphenol A catalyzed by benzenesulfonic acid in the presence of DUOLITE LES 9001 resin C-alkylated by phenol The procedure of Example 8 was repeated, but charging the following reagents;
(i) 7.56 g of phenol (0.08 mol);
(ii) 0.58 g of acetone (0.01 mol);
(iii) 0.56 g of benzenesulfonic acid (0.0035 mol); and
(iv) 2.34 g of resin prepared in accordance with Control Experiment (a) (0.01 mol of phenol).

The analyses of the samples evidenced no effect compared with Control Experiment (b).

The results obtained are reported in Table V below, in which the conventions used are those defined above for Control Experiment (b).

TABLE V

| Time (h) | pp' | op' | BPX | Codimer | Spiro | ΣYY | Q |
|---|---|---|---|---|---|---|---|
| 0.84 | 2.80 | 1.36 | 0.08 | — | — | 4.16 | 0.327 |
| 1.84 | 7.16 | 2.79 | 0.12 | 0.22 | — | 9.95 | 0.280 |
| 3.50 | 15.11 | 4.04 | 0.41 | 1.10 | — | 19.15 | 0.211 |
| 4.42 | 18.54 | 4.67 | 0.56 | 1.43 | — | 23.21 | 0.201 |
| 5.42 | 22.36 | 6.51 | 0.80 | 2.18 | — | 28.87 | 0.225 |
| 6.67 | 28.95 | 7.38 | 0.85 | 2.27 | — | 36.33 | 0.203 |

EXAMPLE 11

Synthesis of bisphenol A catalyzed by benzenesulfonic acid, recycling DUOLITE LES 9001 resin C-alkylated by resorcinol A first experiment was carried out under the conditions of Example 8, but without taking samples. At the end of the experiment (5 hours), the resin was filtered off, washed with phenol and dried, and then employed with the following reagents in a second experiment carried out according to the procedure of Example 8:
(i) 7.56 g of phenol (0.08 mol);
(ii) 0.58 g of acetone (0.01 mol);
(iii) 0.56 g of benzenesulfonic acid (0.0035 mol); and
(iv) 2.55 g of recycled resin.

The analysis of the samples evidenced that the resin still had activity.

The results obtained are reported in Table VI below, in which the conventions used are those defined above for Control Experiment (b).

TABLE VI

| Time (h) | pp' | op' | BPX | Codimer | Spiro | ΣYY | Q |
|---|---|---|---|---|---|---|---|
| 0.25 | 0.99 | 0.28 | 0.06 | — | — | 1.27 | 0.222 |
| 0.50 | 2.36 | 0.48 | 0.06 | — | — | 2.84 | 0.170 |
| 1.34 | 7.67 | 1.26 | 0.08 | — | — | 8.93 | 0.141 |
| 2.00 | 11.57 | 1.70 | 0.05 | — | — | 13.27 | 0.128 |
| 4.00 | 20.54 | 2.81 | 0.28 | 0.12 | — | 23.35 | 0.120 |
| 5.05 | 24.68 | 3.26 | 0.44 | 0.17 | — | 27.94 | 0.117 |
| 6.00 | 28.20 | 3.74 | 0.52 | 0.28 | — | 31.94 | 0.117 |
| 7.34 | 32.70 | 4.03 | 0.65 | 0.39 | — | 36.73 | 0.110 |

Using the results obtained in Examples 8 to 10 and in Control Experiment (b) and (c), the attached ΣYY=f(t) curves (1) to (5) were plotted for each example (or experiment), plotting the time in hours on the abscissas and ΣYY in % on the ordinates.

Curve (1) corresponds to Control Experiment (b) carried out without additive,
Curve (2) corresponds to Example 10,
Curve (3) corresponds to Example 8,
Curve (4) corresponds to Example 9,
Curve (5) corresponds to Control Experiment (a), carried out using an additive not according to the invention.

While the invention has been described in the terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of bisphenol A, which comprises condensing phenol with acetone in the presence of (a) a catalytically effective amount of an acid catalyst and (b) a co-catalytically effective amount of a functional polymer, said functional polymer comprising a polymer backbone having a plurality of functional groups grafted thereon and said functional groups having the formula:

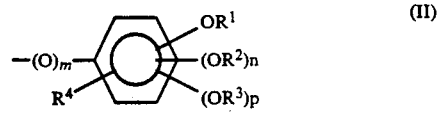

in which m is 0 or 1, n is 0 or 1, p is 0 or 1, $R^1$, $R^2$ and $R^3$, which may be identical or different, are each a hydrogen atom, a $C_1$–$C_6$ alkyl radical or a phenyl radical which is unsubstituted or substituted by 1 or 2 hydroxyl or $C_1$–$C_4$ alkoxy groups, and $R^4$ is a hydrogen atom, a halogen atom, a $C_1$–$C_6$ alkyl radical, or one of the groups: —CHO, —$NO_2$, —$CO_2H$, —$CO_2R^5$ wherein $R^5$ is a $C_1$–$C_4$ alkyl radical, or

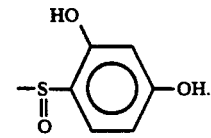

2. The process as defined by claim 1, comprising condensing a stoichiometric excess of phenol with acetone.

3. The process as defined by claim 1, said functional polymer having the formula:

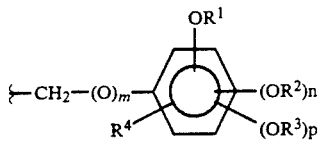 (I)

in which

is the residue of a chloromethylated resin.

4. The process as defined by claim 3, said chloromethylated resin comprising a polystyrene/divinylbenzene polymer.

5. The process as defined by claim 3, at least 90% of the chlorine atoms in said chloromethylated resin having been replaced by functional groups (II).

6. The process as defined by claim 4, said polystyrene/divinylbenzene polymer comprising a BIO-BEAD® S-X1, DUOLITE® LES 9001 or DUOLITE® LES 3781 resin.

7. The process as defined by claim 3, said functional polymer comprising beads thereof 8. The process as defined by claim 3, wherein formula (I), m is 0.

9. The process as defined by claim 8, wherein formula (I), $R^4$ is a hydrogen atom or a $C_1-C_6$ alkyl radical, and $R^1$, $R^2$ and $R^3$, which may be identical or different, are each a hydrogen atom or a $C_1-C_4$ alkyl radical.

10. The process as defined by claim 3, wherein formula (I), at least one of the radicals $R^1$, $R^2$ and $R^3$ is a hydrogen atom and the other two, which may be identical or different, are each a hydrogen atom or a methyl radical.

11. The process as defined by claim 3, wherein formula (I), m is 0, p is 0, $R^4$ is a hydrogen atom or a $C_1-C_6$ alkyl radical, and $R^1$ and $R^2$ are hydrogen atoms, with the proviso that the hydroxyl groups thus formed are on the 2- and 4-positions of the benzene nucleus relative to the methylene bridge.

12. The process as defined by claim 1, wherein the molar ratio of the functional groups (II) to the acetone ranges from 0.1 to 3.

13. The process as defined by claim 1, said acid catalyst comprising benzenesulfonic acid.

14. The process as defined by claim 2, wherein the molar ratio phenol/acetone range from 2 to 16.

15. The process as defined by claim 1, carried out at a temperature ranging from 30° to 120° C.

16. The process as defined by claim 1, wherein the amount of acid catalyst ranges from 0.2 to 0.5 mole per mole of acetone.

17. The product of the process as defined by claim 1.

* * * * *